(12) United States Patent
Florescu

(10) Patent No.: US 9,775,941 B2
(45) Date of Patent: Oct. 3, 2017

(54) HEMODIALYSIS CATHETER WITH DISPLACEABLE LUMENS TO DISRUPT A FIBROUS SHEET

(75) Inventor: Marius C. Florescu, Omaha, NE (US)

(73) Assignee: BOARD OF REGENTS OF THE UNIVERSITY OF NEB, Lincoln, NE (US)

( * ) Notice: Subject to any disclaimer, the term of this patent is extended or adjusted under 35 U.S.C. 154(b) by 207 days.

(21) Appl. No.: 13/993,004

(22) PCT Filed: Dec. 12, 2011

(86) PCT No.: PCT/US2011/064456
§ 371 (c)(1),
(2), (4) Date: Aug. 19, 2013

(87) PCT Pub. No.: WO2012/079083
PCT Pub. Date: Jun. 14, 2012

(65) Prior Publication Data
US 2013/0324964 A1    Dec. 5, 2013

Related U.S. Application Data

(60) Provisional application No. 61/421,842, filed on Dec. 10, 2010.

(51) Int. Cl.
*A61M 1/36* (2006.01)
*A61M 25/00* (2006.01)
*A61M 39/08* (2006.01)
*A61M 25/10* (2013.01)

(52) U.S. Cl.
CPC ........ *A61M 1/3653* (2013.01); *A61M 1/3661* (2014.02); *A61M 25/0032* (2013.01); *A61M 25/0074* (2013.01); *A61M 39/08* (2013.01); *A61M 25/007* (2013.01); *A61M 25/10* (2013.01);
(Continued)

(58) Field of Classification Search
CPC ........ A61M 1/3653; A61M 2025/0031; A61M 2025/0034; A61M 25/0032; A61M 25/0074; A61M 1/3661; A61M 2205/0037; A61M 2025/009; A61M 2025/0091; A61M 2025/0089; A61M 2025/0087;
(Continued)

(56) References Cited

U.S. PATENT DOCUMENTS 4,422,447 A * 12/1983 Schiff ................... A61M 25/10
600/18
5,584,803 A * 12/1996 Stevens ................. A61B 17/29
604/101.01
(Continued)

OTHER PUBLICATIONS

International Search Report and Written Opinion for International Application No. PCT/US2011/064456, dated Jun. 28, 2012.
(Continued)

*Primary Examiner* — Nathan R Price
*Assistant Examiner* — Weng Lee
(74) *Attorney, Agent, or Firm* — Fernandez & Associates, LLP

(57) ABSTRACT

A hemodialysis catheter with an integrated means of displacing away from each other portions of a distal end of a tube assembly. The displacement serves to allow a fibrous sheath to be disrupted without removing the catheter from a patient.

11 Claims, 6 Drawing Sheets

(52) U.S. Cl.
CPC .............. *A61M 2025/0031* (2013.01); *A61M 2025/0034* (2013.01)

(58) Field of Classification Search
CPC .. A61M 2025/0086; A61M 2025/0085; A61M 2025/00; A61M 25/10; A61M 25/0071
See application file for complete search history.

(56) References Cited

U.S. PATENT DOCUMENTS

| | | | |
|---|---|---|---|
| 5,752,934 A * | 5/1998 | Campbell | A61L 29/085 604/96.01 |
| 5,772,642 A * | 6/1998 | Ciamacco et al. | 604/523 |
| 6,692,466 B1 * | 2/2004 | Chow | A61M 25/0084 604/164.01 |
| 2005/0113798 A1 * | 5/2005 | Slater et al. | 604/508 |
| 2005/0245900 A1 | 11/2005 | Ash | |
| 2008/0306427 A1 | 12/2008 | Bailey | |
| 2009/0093748 A1 * | 4/2009 | Patterson | A61M 25/008 604/6.16 |
| 2010/0191165 A1 | 7/2010 | Appling et al. | |
| 2010/0280450 A1 * | 11/2010 | Jain | 604/96.01 |

OTHER PUBLICATIONS

International Preliminary Report on Patentability for International Application No. PCT/US2011/064456, dated Jun. 12, 2013.

* cited by examiner

HEMODIALYSIS CATHETER WITH DISPLACEABLE LUMENS TO DISRUPT A FIBROUS SHEET

CROSS-REFERENCE TO RELATED APPLICATION

This application claims benefit of U.S. Provisional Application No. 61/421,842, filed Dec. 10, 2010, the disclosure of which is hereby expressly incorporated herein by reference.

BACKGROUND

Hemodialysis is a medical procedure that uses an external medical device to clean the blood of people who have experienced complete or partial renal failure. This procedure is typically done 3 times a week and allows patients with renal failure to survive and to lead almost normal lives. Besides kidney transplantation, hemodialysis is the only procedure available today that allows long-term survival of patients with failed kidneys. In the United States, there are approximately 450,000 patients on hemodialysis, and there are approximately 1.7 million patients on hemodialysis worldwide. More than half of the patients starting hemodialysis use a tunneled hemodialysis catheter as a vascular access. Every year in the United States, approximately 500,000 hemodialysis catheter procedures are performed, half of which involve placement or exchange of a hemodialysis catheter. Similarly, there are approximately 2 million hemodialysis procedures performed annually worldwide, most of which involve placement or exchange of the hemodialysis catheter. While a variety of hemodialysis catheters are available, hemodialysis catheters are generally comprised of two tubes, each with a lumen aperture disposed at its end. One tube carries out of the patient blood that needs to be cleaned, while the other returns cleaned blood to the patient.

A common problem with hemodialysis catheters is formation of a fibrous sheath on the exterior surface of the catheter. The name fibrous sheath is somewhat of a misnomer. A mature fibrous sheath (one that has developed for more than 1-2 weeks from catheter insertion) is mainly formed of smooth muscle cells and collagen. The fibrous sheath looks like a thin but resilient layer of material (like cellophane) that surrounds the catheter and blocks the apertures of the lumens, thereby impeding the blood flow needed for an adequate hemodialysis.

A fibrous sheath's composition is very different from that of a thrombus. A thrombus, sometimes referred to as a clot, is composed of blood platelets and results from blood coagulation. Thrombolytic therapy to remove thrombi typically involves the use of medications to dissolve the thrombi. In contrast to thrombi, the above-described fibrous sheaths are composed of smooth muscle cells and collagen, and such fibrous sheaths do not respond to thrombolytic therapy due to the different compositions of fibrous sheaths and thrombi. Instead, other methods are required to disrupt or destroy fibrous sheaths.

Fibrous sheath formation starts as early as 24 hours after insertion of the catheter, and the composition of the fibrous sheath changes as the catheter remains implanted in the patient. The sheath begins as a thrombus in the first few days and rapidly transforms into a combination of smooth muscle cells and collagen deposition covered by endothelial cells after 1-2 weeks. After 4 weeks, the smooth muscle cells change to a contractile phenotype and the amount of collagen deposition is increased.

Fibrous sheaths are known to form around most hemodialysis catheters and also around other devices placed inside the human body such as pacemaker wires, pacemaker boxes, and breast implants. Fibrous sheath formation is especially problematic for implanted catheters that are designed to stay implanted in a patient for months at a time. The fibrous sheath forms around all hemodialysis catheters, causing dysfunction in a significant number of them. In fact, this type of catheter dysfunction accounts for nearly half of all procedures involving the exchange of implanted hemodialysis catheters. In these circumstances, the hemodialysis catheter is removed and the fibrous sheath is obliterated by inflation of an angioplasty balloon inside the sheath. Thereafter, a new catheter is placed inside the patient. This procedure is risky and is very expensive because it is done in sterile conditions, in fluoroscopy (X-ray)-equipped procedure rooms by specially trained doctors and nurses with the patient under conscious sedation.

U.S. Patent Application Publication No. 2008/0306427 A1 describes a catheter device having a shaft, a first lumen extending through the shaft, and a second lumen extending through the shaft. An opening to the first lumen is at a distal end of a shaft and an opening to the second lumen is offset from the opening to the first lumen and positioned further up the shaft in a direction towards a proximal end of the shaft. A balloon is attached to an outer surface of the shaft and is positioned proximate to the opening of the second lumen. The balloon is inflated in an effort to prevent an occluding material from occluding the opening of the first lumen and the opening of the second lumen.

SUMMARY

The present disclosure describes a hemodialysis catheter with an integrated means of displacing away from each other the distal ends of portions of a tube assembly that forms the catheter. The displacement serves to allow a fibrous sheath of tissue formed on the catheter to be disrupted without removing the catheter from the patient. In an embodiment, the fibrous sheath is disrupted by periodic or on-demand inflation of a balloon disposed between two or more portions of the tube assembly proximate to a distal end of the tube assembly.

In one embodiment, a multi-lumen catheter comprises a tube assembly. The tube assembly includes a first portion at a distal end of the tube assembly, and a first lumen extending through the first portion to a first opening at the distal end of the tube assembly. The tube assembly further includes a second portion at a distal end of the tube assembly, and a second lumen extending through the second portion to a second opening at the distal end of the tube assembly. The tube assembly further includes a separation device associated with the first portion and the second portion, wherein the separation device is configured to reversibly separate the first portion from the second portion.

In another embodiment, a method for breaking a fibrous sheath encasing a multi-lumen catheter implanted in a patient comprises operating a separation mechanism to reversibly displace a first portion at a distal end of the catheter from a second portion at the distal end of the catheter with sufficient force to break the fibrous sheath while the catheter is implanted in the patient. The first portion includes a first opening to a first lumen of the catheter and the second portion includes a second opening to a second lumen of the catheter. The method also comprises reversing displacement of the first portion from the second portion.

In yet another embodiment, a method of operating a catheter is provided. The catheter comprises a tube assembly including a first portion at a distal end of the tube assembly, a first lumen extending through the first portion to a first opening at the distal end of the tube assembly, a second portion at a distal end of the tube assembly, a second lumen extending through the second portion to a second opening at the distal end of the tube assembly, and a separation device associated with the first portion and the second portion, wherein the separation device is configured to reversibly separate the first portion from the second portion. The method includes causing the separation device to separate the first portion from the second portion, and causing the separation of the first portion and the second portion to be reversed.

It is to be understood that the foregoing general description and the following detailed description are exemplary and explanatory only, and are not necessarily restrictive of the disclosure. The accompanying drawings, which are incorporated in and constitute a part of the specification, illustrate subject matter of the disclosure and together with the general description, serve to explain the principles of the present disclosure. The disclosure will be understood by those skilled in the art from the following detailed description and drawings.

BRIEF DESCRIPTION OF THE DRAWINGS

The numerous advantages of embodiments of the present disclosure may be better understood by those skilled in the art by reference to the accompanying figures in which.

DETAILED DESCRIPTION

Overview

Fibrous tissue naturally accumulates on the surfaces of implanted hemodialysis catheters over time. This accumulation of fibrous tissue can eventually lead to occlusion of openings in the catheter through which blood flows into and out of the patient. With prior art catheters, this occlusion typically requires the catheter be removed from the patient and replaced. Once the catheter is removed, an angioplasty balloon is typically used to break apart the fibrous tissue. A new catheter is then inserted into the patient once the fibrous tissue is broken apart. The procedure of removing the catheter, breaking apart the fibrous tissue, and replacing the previous catheter with a new catheter is expensive and physically taxing on the patient.

The present disclosure describes embodiments of an apparatus and methods in which a hemodialysis catheter itself is utilized to break at least the portion of the fibrous sheath occluding openings of the catheter. As a result, the accumulated fibrous sheath can be disrupted without removing the catheter. Fibrous tissue formation is a problem that can impact all hemodialysis catheters. While the present disclosure is preferably used in catheters with exit ports that are close to each other (e.g., Covidien AG Tal PALINDROME™; C. R. Bard, Inc. Trialysis™), one of ordinary skill in the art would understand that the present disclosure has broad applicability beyond use in hemodialysis catheters.

Figure 1A:
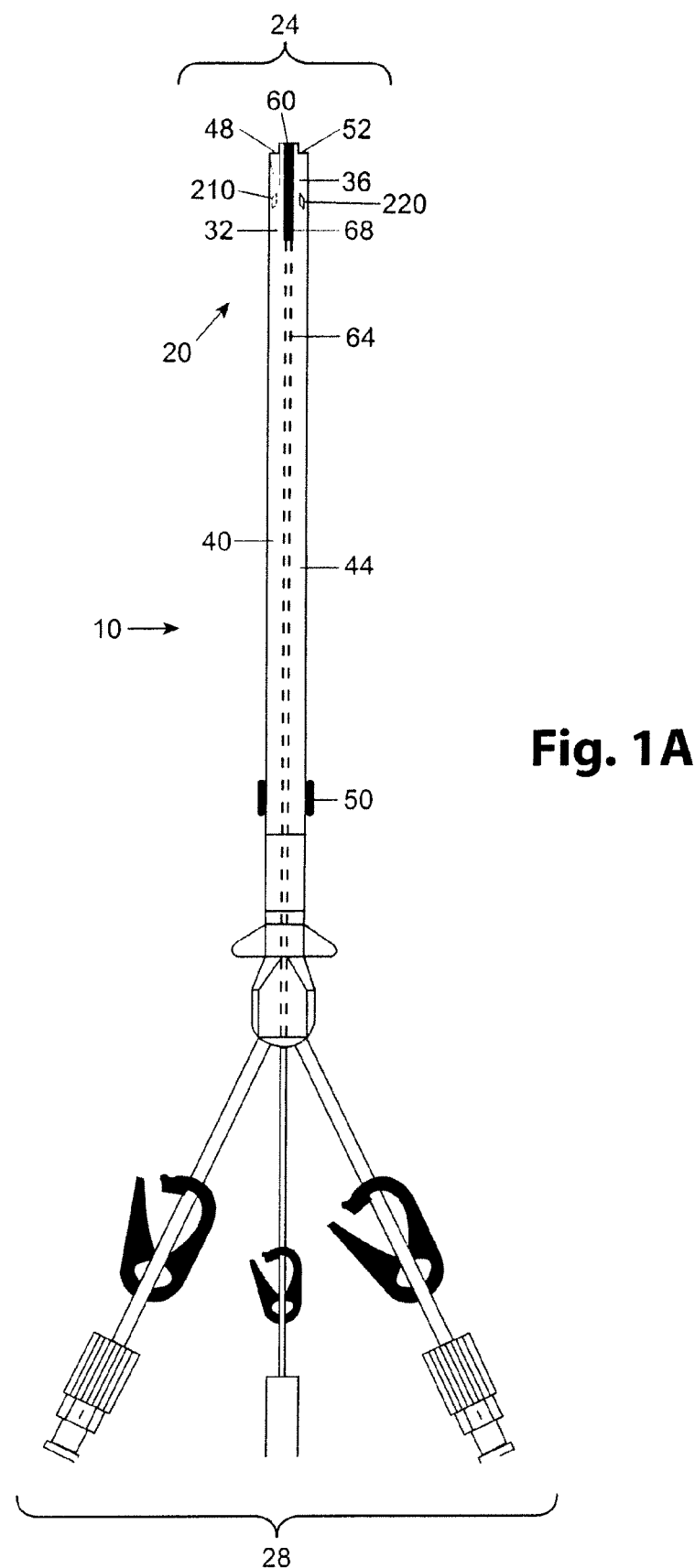
FIGS. 1A and 1B are side elevational views of a catheter, according to an embodiment.
Figure 1B:
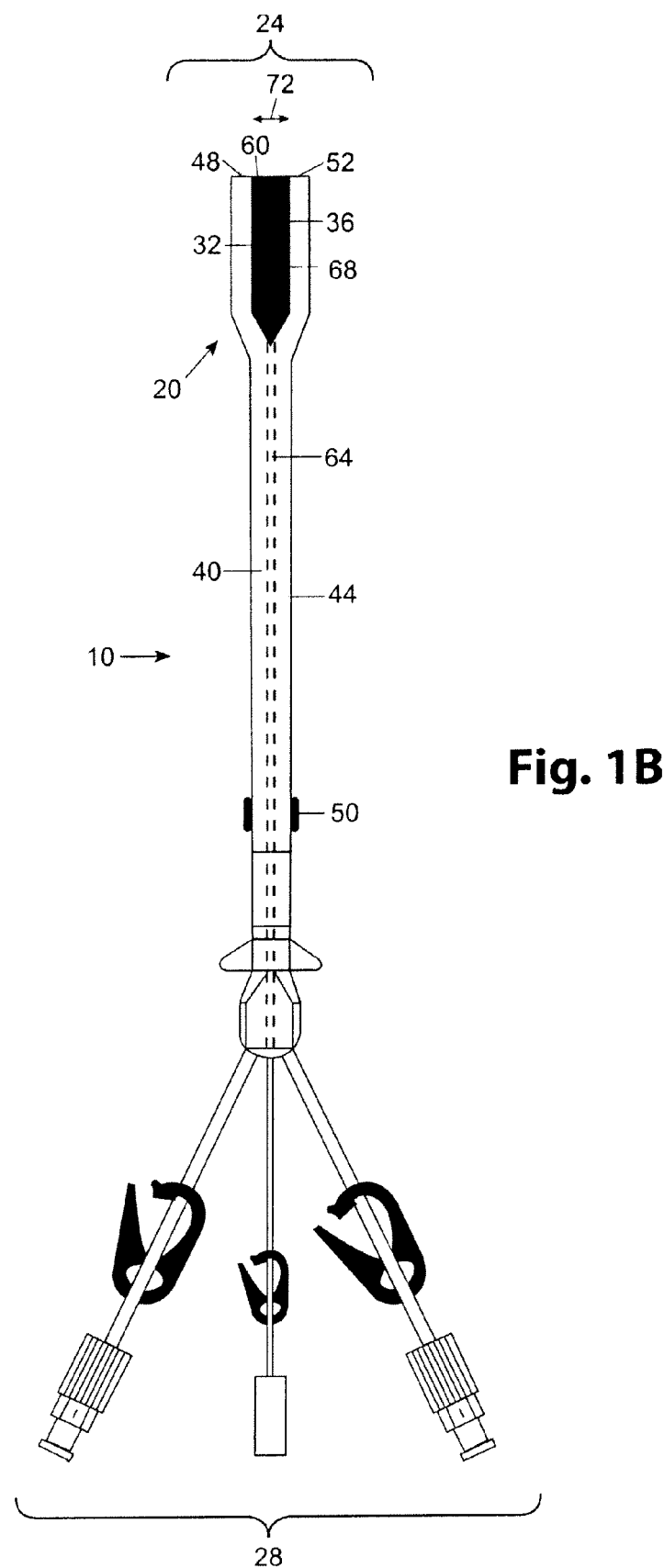

FIGS. 1A and 1B are diagrams of an example hemodialysis catheter device 10, according to an embodiment. The catheter device 10 includes a tube assembly 20 having a distal end 24 and a proximal end 28. The tube assembly 20 includes a first portion 32 and a second portion 36. A first lumen 40 extends through the tube assembly 20, including through the first portion 32. A second lumen 44 extends through the tube assembly 20, including through the second portion 36. The first portion 32 includes a first opening 48 to the first lumen 40, and the second portion 36 includes a second opening 52 to the second lumen 44. The distal end 24 is configured to be implanted within the patient at a suitable location whereas the proximal end 28 is configured to remain external to the patient and to be connected to dialysis equipment. The catheter device 10 also includes a Dacron cuff 50 to help secure the catheter device 10 inside the patient.

The hemodialysis catheter device 10 further includes a separation mechanism to reversibly separate the first portion 32 from the second portion 36. For instance, FIG. 1A illustrates the separation mechanism in a first state, and FIG. 1B illustrates the separation mechanism in a second state. As illustrated in FIGS. 1A and 1B, the first portion 32 and the second portion 36 are more separated from one another when the separation mechanism is in the second state (FIG. 1B). In one embodiment, the separation mechanism causes the first portion 32 and the second portion 36 to separate from one another by at least 5 millimeters (mm) at the distal end 24. In another embodiment, the separation mechanism causes the first portion 32 and the second portion 36 to separate from one another by at least 6 mm at the distal end 24. In another embodiment, the separation mechanism causes the first portion 32 and the second portion 36 to separate from one another by at least 7 mm at the distal end 24. In other embodiments, other suitable separation distances are employed. When the first portion 32 and the second portion 36 are separated from one another by a suitable distance, such as illustrated in FIG. 1B, while the hemodialysis catheter device 10 is implanted in the patient, at least a portion of an accumulated fibrous sheath that has accumulated over the first opening 48 or second opening 52 would be disrupted or obliterated.

In an embodiment, the separation mechanism comprises a balloon 60 positioned between the first portion 32 and the second portion 36. A third lumen 64 extends through the tube assembly 20 to the balloon 60. Fluid is passed through the third lumen 64 to the balloon 60 to cause inflation and deflation of the balloon 60. In an embodiment, the fluid utilized for inflating the balloon comprises a gas. In other embodiments, the fluid may comprise a liquid.

The balloon 60 has characteristics (e.g., pressure rating, volume, dimensions, etc.) suitable for reversibly separating the first portion 32 and the second portion 36 by a desired separation distance. The balloon 60 may fold into a specific form to stay compact when deflated. In an embodiment, the balloon 60 is a standard 7 mm angioplasty balloon. In other embodiments, another suitable balloon may be utilized.

To prevent or minimize contact of the balloon 60 with blood of the patient, a biocompatible material 68 may be utilized, in some embodiments. For example, the balloon 60 may be enclosed, at least partially, in the biocompatible material 68. In an embodiment, the biocompatible material 68 comprises a flexible material. The flexible, biocompatible material 68 may comprise any type of suitable biocompatible material, including, for example, latex. In some embodiments, the biocompatible material 68 may be omitted.

In FIG. 1B, the first portion 32 and the second portion 36 of the hemodialysis catheter 10 are displaced, as indicated by arrows 72, at the distal end 24 by the inflation of the balloon 60. The inflation of the balloon 60 may be accomplished by forcing fluid (e.g., with pressure) through the third lumen 64. The displacement of the first portion 32 and second the second portion 36 may be sufficient to break the fibrous sheath but not large enough to come into contact with the walls of the blood vessel in which the hemodialysis catheter 10 is implanted, at least in some embodiments and/or scenarios. Displacement of the first portion 32 and the second portion 36 is reversible. For example, in an embodiment, when the fluid pressure is removed, the fluid escapes from the balloon 60 via the third lumen 64 and the balloon 60 deflates. As a result of deflation of the balloon 60, the separation of the first portion 32 and the second portion 36 is reversed. In an embodiment that includes a flexible biocompatible cover 68, the flexible biocompatible cover 68 acts to pull the first portion 32 and the second portion 36 together and deflate the balloon 60. In another embodiment, reverse fluid pressure is externally applied so that the fluid is drawn from the balloon 60.

Figure 2A:
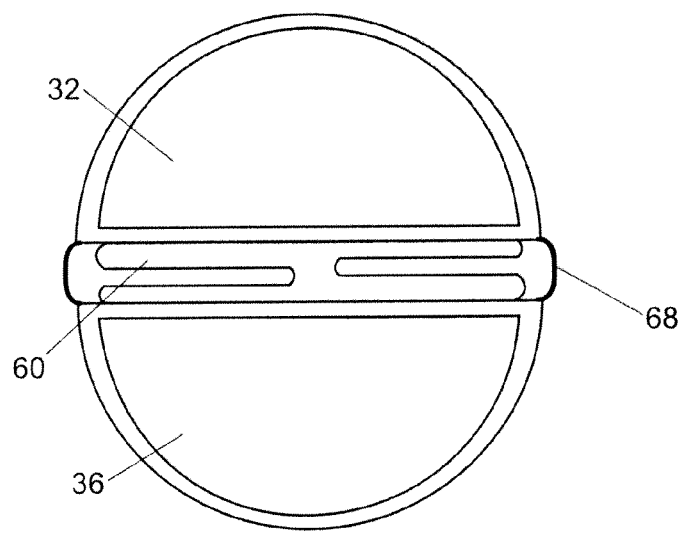
FIGS. 2A and 2B are enlarged cross sectional views of the catheter device shown in FIGS. 1A and 2B.

FIG. 2A is a diagram illustrating a cross section of the distal end 24 of the hemodialysis catheter 10 of FIGS. 1A and 1B when the balloon 60 is not inflated. The first portion 32 and the second portion 36 are in close proximity to one another. The uninflated balloon 60 is disposed between the first portion 32 and the second portion 36 and covered by the flexible material 68.

Figure 2B:
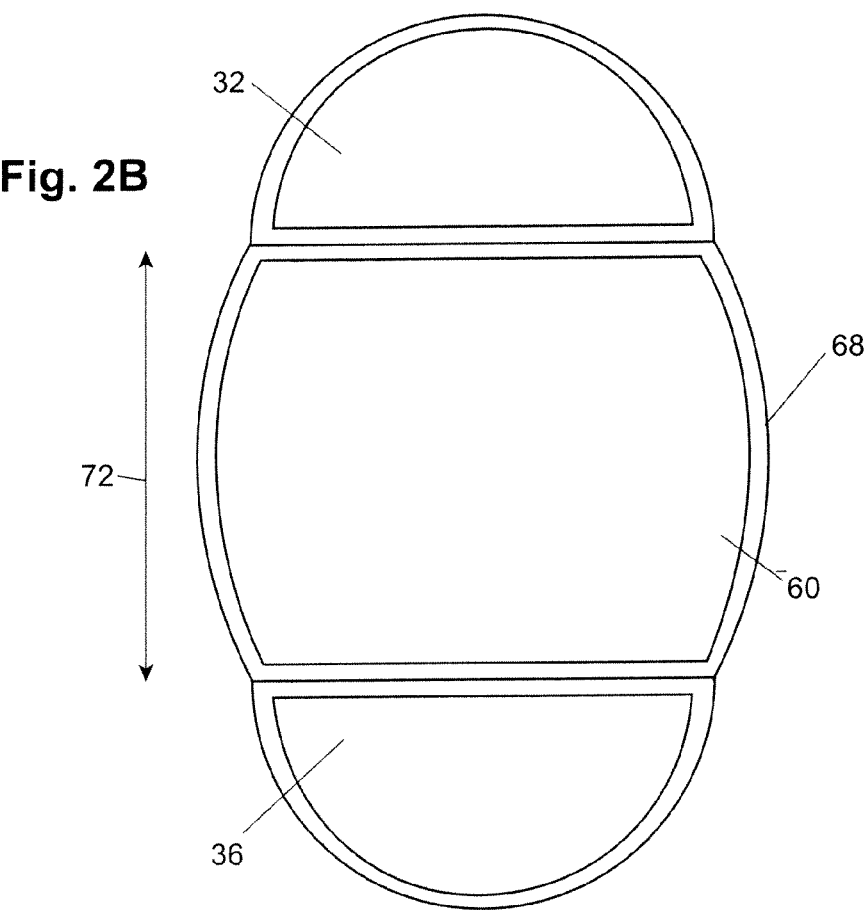

In FIG. 2B the balloon 60 is inflated, displacing, as indicated by the arrows 72, the first portion 32 and the second portion 36 from one another. The flexible material 68 expands with the balloon 60.

In other embodiments, other suitable separation mechanisms are utilized. In one embodiment, a mechanical separation device is disposed between the first portion 32 and the second portion 36. For example, the mechanical separation device may be operable to reversibly change from a compact state to an expanded state. In the expanded state, the mechanical separation device may push the first portion 32 and the second portion 36 apart by a suitable distance. In the compact state, the mechanical separation device may keep the first portion 32 and the second portion 36 substantially together. An activation member coupled to the mechanical separation device may extend to the proximal end of the catheter device 10 to permit a clinician to reversibly change the mechanical device between the compact state and the expanded state. The activation member may extend through a third lumen of the tube assembly 20 and/or external to the tube assembly 20.

In other embodiments, the separation mechanism is not disposed between the first portion 32 and the second portion 36. For example, in some embodiments, a suitable separation mechanism is disposed external to the tube assembly 20 and acts to pull the first portion 32 and the second portion 36 apart from one another.

Figure 3A:
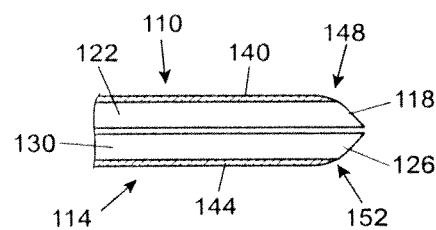
FIGS. 3A-3C are enlarged side views of a distal portion of a catheter according to another embodiment.

FIG. 3A is a diagram of a distal end of an illustrative example of a catheter device utilizing a mechanical separation device disposed at least partially external to the tube assembly, according to another embodiment. A catheter device 10 includes a first portion 110 and a second portion 114 at a distal end, similar to the embodiment of FIGS. 1A and 1B. The catheter device 10 includes a first opening 118 to a first lumen 122, and includes a second opening 126 to a second lumen 130.

Figure 3B:
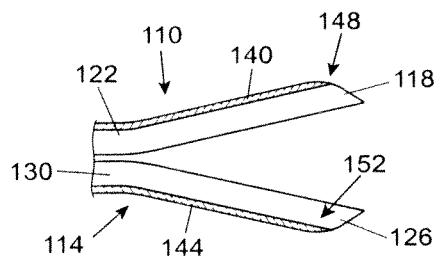
Figure 3C:
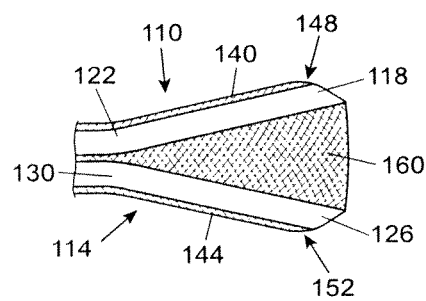

A mechanical separation device is disposed, at least partially, external to a tube assembly of the catheter device 10. For example, the mechanical separation device includes a first member 140 and a second member 144. The first member 140 is attached to the first portion 110 on a side of the first portion 110 that is not adjacent to the second portion 114. The second member 144 is attached to the second portion 114 on a side of the second portion 114 that is not adjacent to the first portion 110. As shown in FIG. 3B, a suitable mechanism, when activated, causes an end 148 of the first member 140 to separate in distance from an end 152 of the second member 144. The first member 140 and the second member 144, in turn, pull apart the first portion 110 and the second portion 114. Deactivation of the mechanism causes the end 148 of the first member 140 to reduce separation in distance from the end 152 of the second member 152. In turn, separation of the first portion 110 and the second portion 114 from one another is reversed. As shown in FIG. 3C, a flexible, biocompatible material 160 may be included to cover at least the area between the first portion 110 and the second portion 114 when the separation mechanism is activated, thereby reducing the likelihood of thrombosis. Furthermore, in some embodiments, the flexible, biocompatible material 160 would tend to return to an unstretched state, thereby facilitating reversing the separation of the first portion 110 and the second portion 114.

Figure 4:
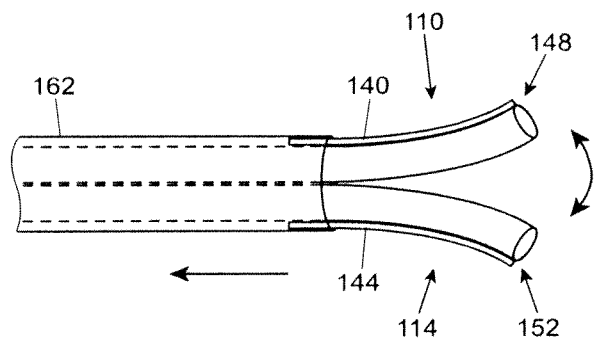
FIG. 4 is a diagram of a catheter utilizing a mechanical separation device, according to an embodiment.

FIG. 4 is a diagram of a catheter utilizing a mechanical separation device, according to an embodiment. In this embodiment, the first member 140 and the second member 144 are made of a deformable material, such as a suitable metal or plastic. The first member 140 and the second member 144 are shaped such that the first member 140 and the second member 144, when in their steady-state position, work to separate the first portion 110 and the second portion 114. A holding sheath 162 is used to reverse this separation by sliding along a portion in the direction of the distal end 24 of the catheter device 10 (shown in FIGS. 1A and 1B) and causing the first member 140 and the second member 144 to deform to a substantially straight position.

Figure 5:
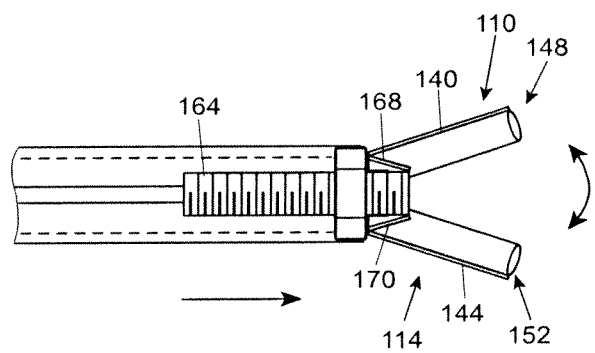
FIG. 5 is a diagram of a catheter utilizing a mechanical separation device, according to another embodiment.

FIG. 5 is a diagram of a catheter utilizing a mechanical separation device, according to another embodiment. In this embodiment, the separation device includes a rotatable threaded portion 164 used to cause the first member 140 and the second member 144 to reversibly separate. In particular, the first member 140 is coupled a first separation portion 168, or the first separation portion 168 is an integral part of the first member 140. Similarly, the second member 144 is coupled a second separation portion 170, or the second separation portion 170 is an integral part of the second member 144. As the rotatable threaded portion 164 rotates in a first direction, the rotatable threaded portion 164 moves toward the distal end of the catheter and the rotatable threaded portion 164 pushes the first separation portion 168 of the first member 140 and the second separation portion 170 of the second member 144. As the first separation portion 168 and the second separation portion 170 are pushed toward the distal end of the catheter, the first member 140 and the second member 144 are caused to separate. On the other hand, as the rotatable threaded portion 164 rotates in a second direction, the rotatable threaded portion 164 moves away from the distal end of the catheter. In an embodiment, the first member 140 and the second member 144 are under tension, e.g., by a spring (not shown), such that as the rotatable threaded portion 164 moves away from the distal end of the catheter, the first member 140 and the second member 144 reverse separation. In another embodiment, the rotatable threaded portion 164 is coupled to the first separation portion 168 of the first member 140 and the second separation portion 170 of the second member 144, such that as the rotatable threaded portion 164 moves away from the distal end of the catheter, the rotatable threaded portion 164 pulls the first separation portion 168 and the second separation portion 170 away from the distal end of the catheter, causing the first member 140 and the second member 144 to reverse separation. A rotation member (not shown) is coupled to rotatable threaded portion 164 and may extend to the proximal end of the catheter device 10 to permit a clinician to cause the rotatable threaded portion 164 to rotate. The rotation member may be manually rotated or rotated using a motor in some embodiments.

Figure 6:
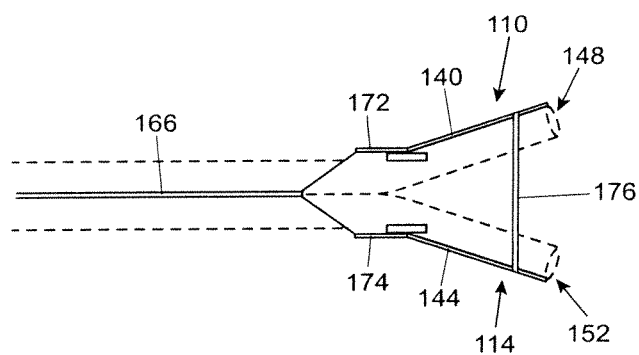
FIG. 6 is a diagram of a catheter utilizing a mechanical separation device, according to yet another embodiment.

FIG. 6 is a diagram of a catheter utilizing a mechanical separation device, according to another embodiment. The first member 140 is coupled to a first rotating portion 172, or the first rotating portion 172 is an integral part of the first member 140. Similarly, the second member 144 is coupled a second rotating portion 174, or the second rotating portion 174 is an integral part of the second member 144. A translating member 166 is coupled to first rotating portion 172 and the second rotating portion 174. The translating member 166 may extend to the proximal end 28 of the catheter device 10. As the translating member 166 is pulled toward the proximal end 28 of the catheter device 10, the rotating portions 172, 174 are caused to rotate. This rotation causes the first member 140 and the second member 144 to separate. On the other hand, as the translating member 166 is pulled toward the proximal end 28 of the catheter device 10, the rotating portions 172, 174 are caused to rotate in an opposite direction causing the separation of the first member 140 and the second member 144 to reverse.

The separation devices such as described above may be actuated using suitable electromechanical devices integral with the catheter device 10. For example, with respect to FIG. 4, a linear actuator may be coupled to the sheath 162 and may be utilized to slide the holding sheath back and forth (i.e., away from and towards the distal end) to respectively separate the first portion 110 and second portion 114 or force the first portion 110 and second portion 114 together. Also, with respect to FIG. 6, a linear actuator also may be coupled to the rotating portions 172, 174 to pull the first portion 110 and the second portion 114 apart. With respect to FIG. 5, a rotary actuator (e.g., a motor) may be coupled to the rotatable portion 164 to rotate the rotatable portion 164 in the first direction and the second direction, thereby causing the first portion 110 and the second portion 114 to be pulled apart, or pushed together. Each of the actuators could be located external to the patient or integrated into the catheter device 10 and placed inside the patient.

In the embodiments of FIGS. 4-6, the first member 140 is attached to the first portion 110 on a side of the first portion 110 that is not adjacent to the second portion 114, and the second member 144 is attached to the second portion 114 on a side of the second portion 114 that is not adjacent to the first portion 110. In other embodiments, similar first and second members are attached to adjacent sides of the first portion 110 and the second portion 114, and such similar first and second members are moved apart from each other to cause separation of the first portion 110 and the second portion 114 by pushing the first portion 110 and the second portion 114 apart.

In each embodiment of the present disclosure (including the embodiments of FIGS. 1A and 1B), to help prevent trauma to the superior vena cava (SVC) caused by over-separating the first portion 110 and the second portion 114, a limiting device 176, such as is shown in FIG. 6, may be employed. The limiting device 176 may take the form of a link (e.g., a string, a chain, etc., made of a suitable biocompatible material) between and coupled to the first portion 110 and the second portion 114 that limits separation of the portions, as shown in FIG. 6. Alternatively, the limiting device may take the form of a mechanical stop used in the above described mechanical and electromechanical embodiments of the separation device.

Figure 7:
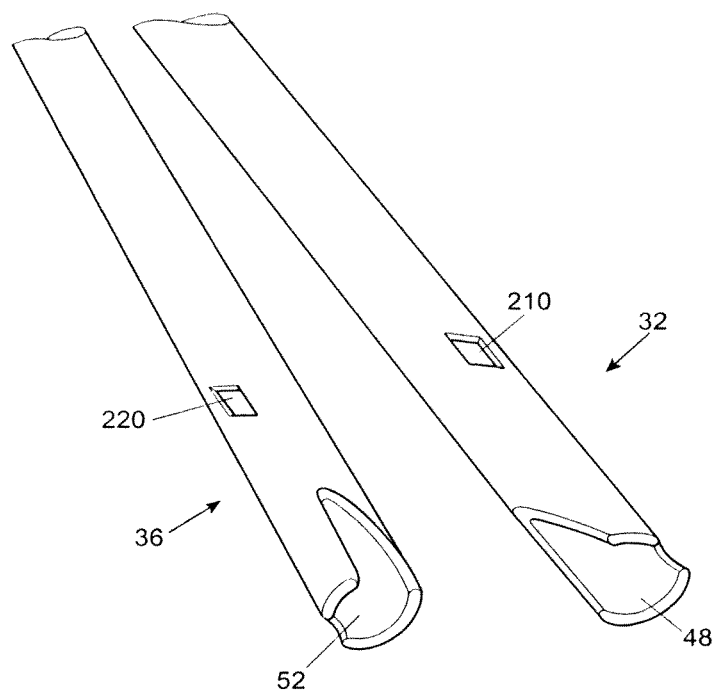
FIG. 7 is a diagram of a first portion and a second portion at a distal end of a catheter, according to an embodiment.

FIG. 7 is a diagram of the first portion 32 and the second portion 36 of the catheter device 10 of FIGS. 1A and 1B, according to an embodiment. The first portion 32 includes an exit port 210, and the second portion 36 includes an exit port 220. The first portion 32, at the first opening 48, is shaped as depicted in FIG. 7. Similarly, the second portion 36, at the second opening 52, is shaped as depicted in FIG. 7. In other embodiments, the first opening 48 and the second opening 52 have different suitable shapes. In some embodiments, the second opening 52 is offset from the first opening 48 along the tube assembly in a direction toward the proximal end of the catheter device. Thus, in other embodiments, a catheter device includes suitable a first portion 32 and a suitable second portion 36 different than depicted in the figures.

Although embodiments were described above in the context of catheter devices having two lumens utilized for blood flow, in other embodiments, catheter devices include more than two lumens and more than two portions at the distal end via which the lumens extends. In these embodiments, a suitable separation mechanism is utilized to cause the more than two portions at the distal end of the catheter to reversibly separate from one another.

Although a few exemplary embodiments of the present disclosure have been shown and described, the present disclosure is not limited to the described exemplary embodiments. Instead, it would be appreciated by those skilled in the art that changes may be made to these exemplary embodiments without departing from the principles and spirit of the present disclosure, the scope of which is defined by the claims and their equivalents.

What is claimed is:

1. A hemodialysis catheter comprising exactly three lumens with a separation device for disrupting a fibrous sheath while inserted in a vein comprising;
   a tube assembly including;
   a first portion at a distal end of the tube assembly;
   a first lumen extending through the first portion to a first opening at the distal end of the tube assembly;
   a second portion at a distal end of the tube assembly;
   a second lumen extending through the second portion to a second opening at the distal end of the tube assembly wherein the first and second lumens are not in communication with each other;
   a separation mechanism; and
   a third lumen extending through the tube assembly to the separation mechanism; wherein the separation mechanism is associated with the first portion and the second portion such that the separation mechanism is configured to reversibly separate the first portion from the second portion such that the first lumen is separated from the second lumen by at least 5 mm proximate to the distal end of the tube assembly, further causing the fibrous sheath to be disrupted and wherein the third lumen comprises a biocompatible material encasing the separation mechanism such that the separation mechanism is not exposed to the interior of the vein.

2. The catheter of claim 1, wherein the separation mechanism comprises one of a balloon, a mechanical separation device comprising a rotatable threaded portion or a mechanical separation device comprising an activation portion.

3. The catheter of claim 2, wherein the balloon is expandable to a diameter of at least 5 mm.

4. The catheter of claim 2, wherein the balloon is expandable to a diameter of at least 6 mm.

5. The catheter of claim 2, wherein the third lumen is operable to provide a fluid to the separation mechanism.

6. The catheter of claim 1, further comprising a flexible bio-compatible material to cover at least the separation mechanism.

7. The catheter of claim 6, wherein the flexible biocompatible material comprises latex.

8. The catheter of claim 1, wherein the separation mechanism comprising a rotatable threaded portion is operable such that when rotated in a first direction, causes the first portion and the second portion to separate, and, when rotated in a second direction, causes separation of the first portion and the second portion to reverse.

9. The catheter of claim 1 further comprising a limiting device coupled to the first portion and the second portion.

10. The catheter of claim 8 further comprising a limiting device coupled to the first portion and the second portion.

11. The catheter of claim 1 wherein the separation mechanism is substantially enclosed between the first lumen and the second lumen such that the separation mechanism is operable to reversibly separate the first portion from the second portion by at least 5 mm.

* * * * *